(12) United States Patent
Gingold et al.

(10) Patent No.: US 6,327,336 B1
(45) Date of Patent: Dec. 4, 2001

(54) RADIOGRAM SHOWING LOCATION OF AUTOMATIC EXPOSURE CONTROL SENSOR

(75) Inventors: Eric Gingold, Bala Cynwyd, PA (US); James K. Merello, Elkton, MD (US); Gregory F. Powell, Bear, DE (US)

(73) Assignee: Direct Radiography Corp., Newark, DE (US)

( * ) Notice: Subject to any disclaimer, the term of this patent is extended or adjusted under 35 U.S.C. 154(b) by 0 days.

(21) Appl. No.: 09/587,022

(22) Filed: Jun. 5, 2000

(51) Int. Cl.[7] .................................................. H05G 1/64
(52) U.S. Cl. ......................................... 378/98.7; 378/108
(58) Field of Search ................................. 378/95, 96, 97, 378/98.7, 108, 109, 110, 111, 112, 207, 162, 205

(56) References Cited

U.S. PATENT DOCUMENTS

| | | |
|---|---|---|
| 4,845,771 | 7/1989 | Wislocki et al. ...................... 378/97 |
| 5,084,911 | 1/1992 | Sezan et al. ............................ 378/96 |
| 5,179,582 | 1/1993 | Keller et al. ............................ 378/96 |
| 5,313,206 | 5/1994 | Davies et al. ......................... 341/156 |
| 5,331,166 | 7/1994 | Yamamoto et al. ............. 250/370.11 |
| 5,461,658 | 10/1995 | Joosten ................................ 378/98.7 |
| 5,648,660 | 7/1997 | Lee et al. ......................... 250/370.09 |
| 5,909,478 | 6/1999 | Polichar et al. .................... 378/98.2 |
| 6,175,614 * | 1/2001 | Jensen et al. ....................... 378/98.7 |
| 6,198,800 * | 3/2001 | Garland et al. .................... 378/98.7 |
| 6,208,710 * | 3/2001 | Nagai ................................... 378/108 |

* cited by examiner

*Primary Examiner*—David P. Porta
(74) *Attorney, Agent, or Firm*—Ratner & Prestia

(57) ABSTRACT

A method for optimizing the radiogram image of a subject is provided. The method provides for showing the location of automatic exposure control sensors on the radiograms, along with alignment and targeting projections to optimize the radiation exposure of the subject. By displaying the location of the automatic exposure control sensors on the radiograms along with the image of the subject, the observers can determine whether the radiogram image was taken with appropriate subject alignment. This method also serves as an educational aid in training radiography technicians.

4 Claims, 3 Drawing Sheets

RADIOGRAM SHOWING LOCATION OF AUTOMATIC EXPOSURE CONTROL SENSOR

BACKGROUND OF THE INVENTION

1. Field of the Invention

This invention relates to electronic radiography and more particularly to automatic exposure control systems and methods.

2. Description of Related Art

Electronic radiographic imaging, also commonly referred to as direct radiographic imaging, using imaging panels comprising a two dimensional array of minute sensors to capture a radiation generated image is well known in the art. Information representing an image is captured, usually as a charge distribution stored in a plurality of charge storage capacitors, in individual sensors arrayed in a two dimensional matrix. Readout of the stored charges provides an electrical signal which may be used to display the captured charges as a radiographic image on a display device, such as a cathode ray tube.

In a typical arrangement, an X-ray radiation source is used to provide a radiation beam. The radiation beam is aimed at an imaging panel at a known and usually fixed position, spaced from the source. A patient is positioned in front of the imaging panel between the imaging panel and the radiation source so that the radiation beam passes through the patient's body before impinging thereon.

The patient's body absorbs and scatters a certain amount of the radiation modulating the radiation intensity exiting the body and impinging on the imaging panel. The modulated radiation generates charges in the array of the sensors forming the panel in proportion to its intensity and the time during which the radiation impinges on the panel.

The duration of radiation emission is critical in generating an image having optimum diagnostic characteristics. If the time is too long the results will be unnecessarily high radiation dose to the patient and possible saturation of the detector. If the time is too short, the results will be lack of detail in certain areas, as well as excessive quantum noise (mottle) in the image. In some cases the radiographic examination may need to be repeated, exposing the patient to additional radiation, as well as delaying the evaluation of the examination results and increasing the cost of the procedure.

The solution to this problem is an automatic exposure control system in which the radiation intensity through the patient is monitored and the exposure terminated after a certain time resulting in a desired exposure of the imaging panel to the impinging radiation. Such systems typically use one or more radiation sensors placed in front of, or behind, the panel to measure the amount of incident radiation impinging on the sensor generating an electrical output proportional to the radiation intensity. This output is integrated over time and when a preset limit is reached the radiation source is turned off and the exposure terminated. See for instance U.S. Pat. No. 5,331,166 issued in 1994 to Yamamoto et al. and/or U.S. Pat. No. 5,461,658 issued Oct. 24, 1995 to Joosten for typical exposure control systems used with electronic or direct radiography imaging systems.

A problem with most prior art systems that rely on intensity integration is that the intensity of the radiation incident on the control sensor depends on the relative position of the patient and the sensor. If it is intended that the patient and sensor be so positioned that the sensor receives radiation passing through soft tissue only, placing the patient improperly may result in radiation passing through bone rather than soft tissue prior to impinging on the sensor. In such case, it is obvious that the exposure will no longer be optimal since the sensor will control the duration of the exposure assuming that it is receiving radiation passing through soft tissue rather than bone.

In an effort to minimize this problem, radiation sources have been developed with associated patient placement aids. Typical of such aids are projection systems that project a visual pattern aligned with the radiation beam onto the patient, such as a luminous field and/or a crosshair. The technician places the patient so that the pattern falls into predefined areas of the patient's anatomy. Other systems provide markings on the surface supporting the patient or the imaging panel, indicating the position of the exposure control sensor thereunder, so that the patient may be properly placed to allow for optimum operation of the system.

More complex systems using multiple inputs from a plurality of sensors, or systems analyzing the output of imaging sensors have also been developed in an effort to obtain optimum exposure. U.S. Pat. No. 5,084,911 issued to Sezan et al. exemplifies such a system where proper exposure is calculated by selecting one or more signals from the imaging panel array of X-ray sensors and calculating exposure using the selected signals.

However, none of the prior art systems allow the technician or doctor to determine when viewing a displayed image whether a less than optimal exposure is the result of system failure or poor patient positioning relative to the exposure control sensor or sensors. Such determination is very useful both in calibrating the exposure system and in training radiology technicians in proper patient placement and in diagnosing the cause of incorrect or sub-optimal exposure levels. There is thus still a need for a system that will indicate the relative position of the exposure control sensor or sensors during exposure after the exposure is terminated.

SUMMARY OF THE INVENTION

Providing the ability to optimize exposure by knowing the location of the control sensor during a prior exposure is an object of the present invention.

The above object is obtained by a method applicable in direct radiography of a subject having areas presenting different radiation absorption, in an imaging system comprising a radiation detection imaging panel having a plurality of elemental sensors that provides an electrical output signal representative of the radiation intensity incident on said imaging panel. The system further includes a radiation source, and an exposure control system. The exposure control system comprises at least one exposure control sensor positioned to receive radiation transmitted through the subject. The method comprises:

(a) exposing the subject to radiation for a time controlled by the exposure control system;

(b) capturing with said imaging panel the exposure of the subject as an electrical signal representing a radiogram; and (c) displaying the radiogram on the display medium simultaneously with indicia superposed on the radiogram showing the relative location on the radiogram of the at least one exposure control sensor.

The above method may be implemented in a system comprising:

(a) an imaging panel having a plurality of elemental sensors providing an electrical output signal representative of the radiation intensity incident on the imaging panel;

(b) an imaging radiation source;

(c) an exposure control system including at least one exposure control sensor positioned to receive radiation incident on said panel, the exposure control system connected to said imaging radiation source and said imaging panel;

(d) an image display device; and (e) an electronic image processor connected to the imaging panel and to the image display device;

wherein the image processor processes the output from the imaging panel to display an image representing a radiogram of a subject located between the radiation source and the panel and superposes on the displayed radiogram indicia showing the position of the at least one control sensor relative thereto.

BRIEF DESCRIPTION OF THE DRAWINGS

The invention can be more fully understood from the following description thereof in connection with the accompanying drawings described as follows.

DESCRIPTION OF THE PREFERRED EMBODIMENT(S)

Figure 2:
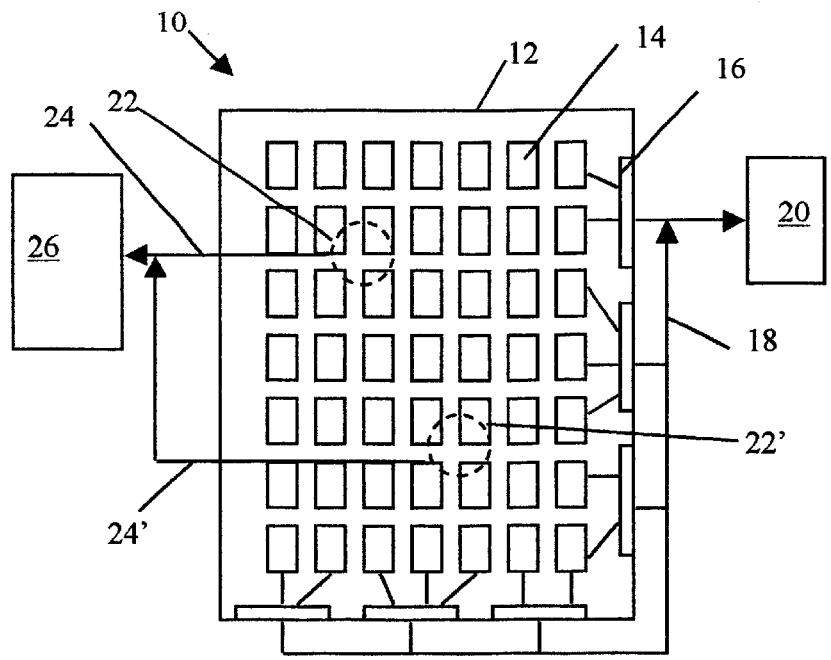
FIG. 2 shows a typical imaging panel and sensor array in accordance with this invention together with an automatic exposure control system having two control sensors located behind the panel.

Throughout the following detailed description, similar reference characters refer to similar elements in all figures of the drawings.

Figure 1:
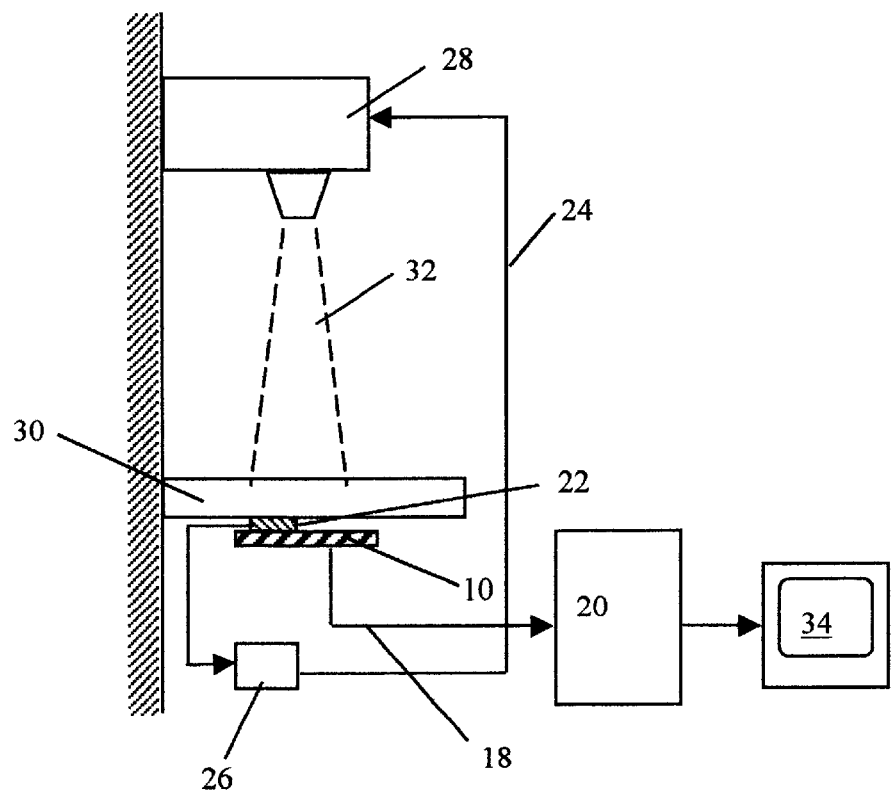
FIG. 1 shows a typical radiographic exposure system and its components.

Referring now to FIG. 1, there is shown a typical radiographic installation for obtaining an electronic radiogram of a patient. The system typically includes a radiation source and a patient support table 30. The radiation source 28 emits on command x-rays as an x-ray radiation beam 32 directed toward a predetermined area of the table 30. Beneath the table 30 in the area where the radiation beam 32 is directed, there is an imaging panel 10. The imaging panel comprises a plurality of individual radiation detectors each corresponding to one picture element, typically arrayed in a two dimensional array. The array of sensors forms an image sensitive area over which a subject to be examined is placed.

The imaging panel 10 usually includes along at least one edge thereof a plurality of electronic components for addressing each individual sensor in the panel, and for detecting and amplifying the electrical signal from the sensors. The imaging panel 10 is semi-permanently mounted under the table 30 and is electrically connected to a controller 20.

Controller 20 performs a number of functions primarily determined by the nature of the electronic imaging panel 10 and may comprise more than one component. The controller 20 typically includes a computer programmed to drive the panel 10 and associated electronics to capture a radiogram and to retrieve and process the signal captured by the detector so that such signal may be displayed on a monitor 34 as a radiogram substantially the same as a traditional radiogram obtained by exposing and developing photographic film. Such controllers and image processors are well known in the art.

The signal retrieved from the panel usually undergoes image processing in the computer, to reduce noise, equalize the output of the individual sensors, replace defective elements, etc. U.S. Pat. Nos. 5,313,206 and 5,648,660 both issued to Lee et al. and assigned to the assignee of the present invention show a typical direct radiation detector panel and associated circuitry for signal recovery.

The system shown in FIG. 1 includes automatic exposure control, shown as comprising at least one exposure control radiation sensor 22 placed in front of the imaging panel 10 in the path of the radiation beam 32. The exposure sensor 22 is connected to an exposure calculator 26 which in turn over wiring 24 is connected to the radiation controller and x-ray source 28.

The exposure control sensor 22 typically generates a charge as a result of the incident radiation. The calculator 26 integrates the charge and when it reaches a preset magnitude it sends a signal to the X-ray generator controller which in turn de-energizes the x-ray source.

FIG. 2 is a schematic representation of a top view of an imaging panel 10 comprising a plurality of individual radiation sensors 14 arrayed in an x-y pattern within a cassette enclosure 12. The individual sensors are connected to address and charge recovering electronic components 16 which in turn are connected to controller 20 over wiring 18.

Shown in dotted lines are two exposure control sensors 22 and 22' connected over wiring 24 and 24' to exposure calculator 26. While two sensors are shown only one may be used or again more than two. The sensors are usually fixed in position relative to the array of detectors 14. However either the array detector or the sensors may be able to be repositioned relative to each other. The sensors may be moveable, or the radiation detector may be rotated 90°.

In accordance with the present invention, the position of the exposure control sensors relative to the individual pixel detectors of the imaging panel 10 is determined and stored. Preferably the position and outline of the detector area of the imaging panel is identified in terms of x-y coordinates. The same co-ordinate system can be used for identifying the position of each individual detector in the imaging panel, as well as the position of the exposure control sensors. The position of the exposure control sensor may alternatively be identified by the individual detectors located directly beneath the exposure control sensor. The exposure control sensor may also be identified by any other means that permit creating indicia representing the exposure control sensor in its exact position on the image captured and displayed by the imaging panel 10 detectors.

The information identifying the location of the exposure control sensor or sensors relative to the detector array may be obtained once for fixed installations and stored in a memory for later use. This is appropriate when the relative position of the panel and the control sensor is not expected to change. Alternatively, when the exposure control sensor is moveable, a tracking system may be used to record the sensor's relative position with respect to the underlying array of detectors. The tracking system would trace the exposure control sensor position in a similar manner as a pointer position on a computer screen is tracked when a driving tool such as a mouse is moved along a pad.

Figure 3:
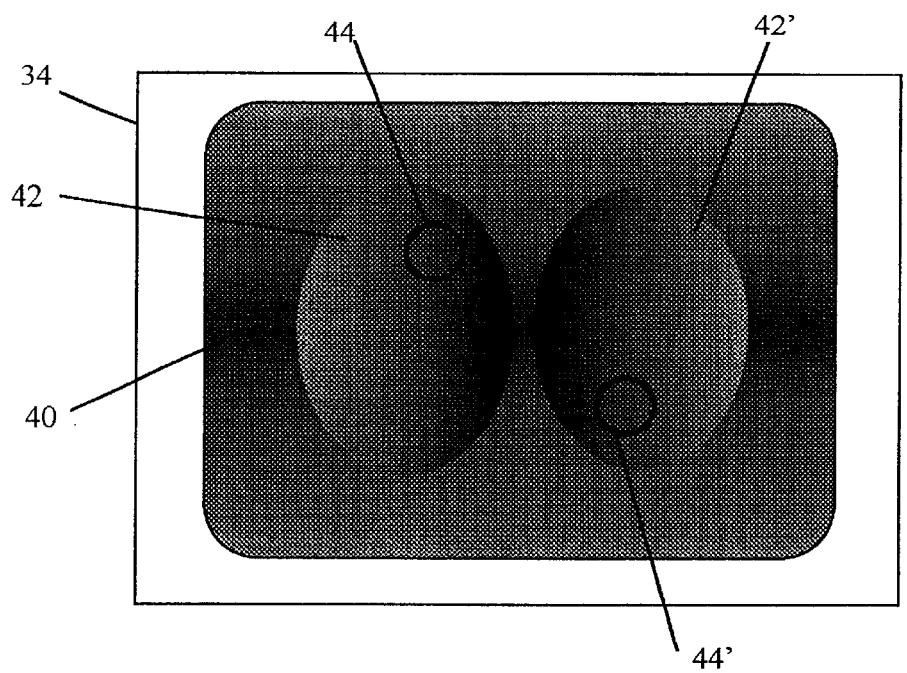
FIG. 3 shows a stylized displayed radiogram with superposed exposure sensor indicia according to this invention.

FIG. 3 is a stylized representation of a displayed radiogram 40 having different density areas as would be the case of a frontal chest x-ray exposure. The oval areas 42 and 42' may be imagined to represent the two lung areas separated by the metadiastinum, which is bone and typically absorbs more radiation than the surrounding areas. Without the two circles 44 and 44', it is impossible to tell where the exposure control sensors were located when viewing this radiogram. It is therefore impossible to discern whether the exposure control sensor was located in the more transparent tissue area or in the more absorbing area under the bone.

According to the present invention, there is superposed on the radiogram two circles 44 and 44' representing two exposure control sensors relative to the captured image. The location of the sensors can be displayed on the image because the position of the sensors was recorded relative to the image capturing detectors. With the sensors' positions displayed, the observer has the ability to immediately determine whether the patient was correctly positioned. For instance, if the exposure was set to produce optimum soft tissue images, one may immediately observe whether the sensors were indeed under the transparent tissue areas or not.

The indicia of the exposure control sensors may take any desired or convenient form. They can represent an outline of the actual exposure control sensor area, or may be a crosshair indicator. The indicia may be black or white or colored.

Figure 4:
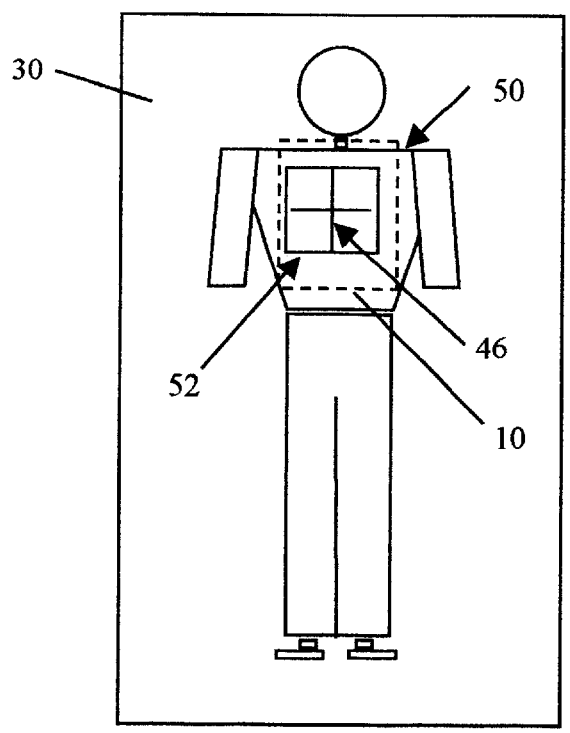
FIG. 4 shows a patient placed in position for a radiographic exposure and a visible pattern projected onto the patient for aligning the patient relative to the radiation beam.

The indicia of the exposure control sensors may be used in combination with other alignment or positioning mechanisms. A targeting alignment device may be used to provide a visible projected pattern on the subject. Most modern x-ray exposure systems provide a visual aid to assist the placement of a patient relative to the radiation beam known as an illuminated collimating field. FIG. 4 shows one such field which takes the form of a visible outline of the exposure field 52 that is projected onto the patient. The visible projection may also be a crosshair 46 or a combination of the two, or any other type of indication that permits the technician operating the equipment to place the patient in the right position relative to the radiation beam.

Figure 5:
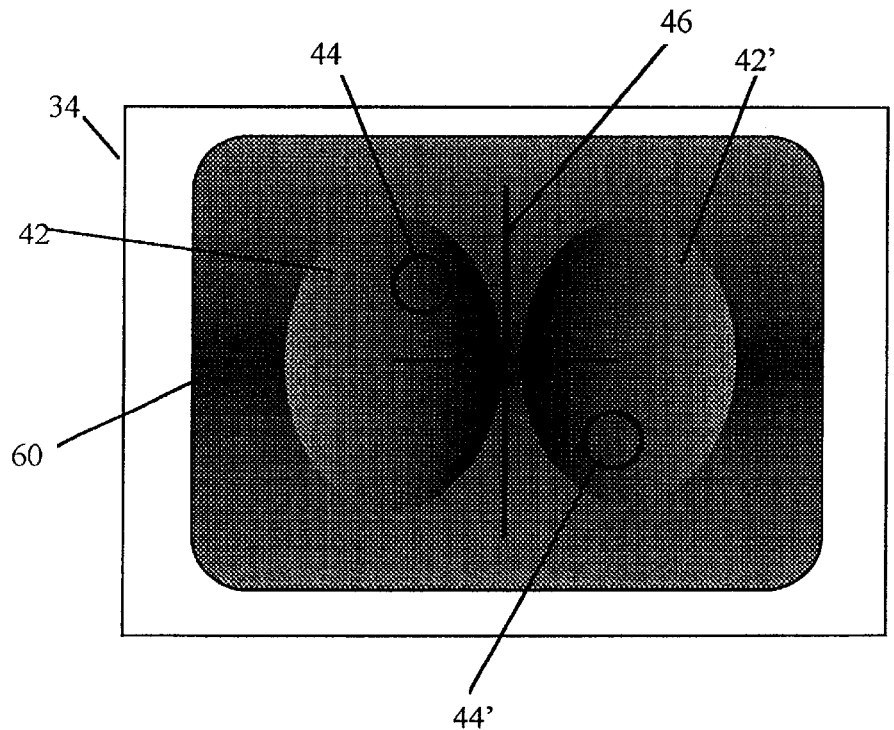
FIG. 5 shows a stylized displayed radiogram in accordance with this invention wherein both the alignment pattern and control sensor positions are shown superposed on the displayed image.

The location of a projected image representing the exposure field may also be determined relative to the imaging panel array (50). The exposure field location information can be stored and displayed 46 superposed on the radiogram as shown in FIG. 5 where a radiogram 60 is shown. Displaying the exposure field projected image with the patient radiogram can be useful in training the technician in proper patient placement, as well as a useful guide in repositioning the patient after an improper initial radiogram.

Figure 6:
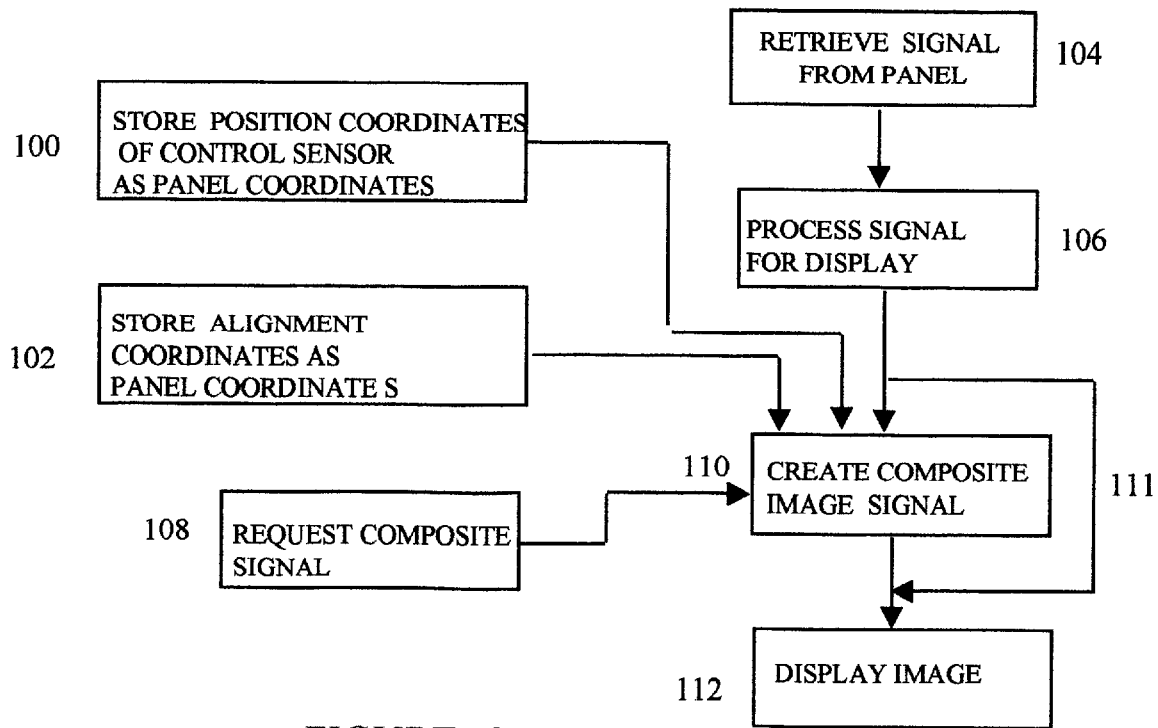
FIG. 6 shows a flow diagram of a software implementation of the steps required to perform the present invention.

The method of the present invention may be implemented using software to program the computer 20 to display the assorted images simultaneously. This technology, superposing two or more images, is well known in the art and needs not further detailed explanation. The position information of the exposure control sensor and, if desired, the outline of the control sensor area is incorporated through the software program outlined in FIG. 6. The exposure control sensor position and area information is first obtained and stored in a memory (100). This information can be initially obtained by lining the exposure control sensors with a small wire and taking a x-ray image to determine the location.

Optionally the collimator field visual aid mark or marks may also be obtained and their position stored in memory (102). Wire(s) may also be employed to determine the location of the visual aid mark by placing a small wire along the projected image, and collecting an x-ray image.

Once position information has been stored and an exposure has been completed, the signal from the detector array panel is retrieved (104). The signal is then amplified, digitized and processed for gain equalization and bad pixel information (106). The signal may undergo a number of further processing steps and may be stored in memory for retrieval and display or may be displayed immediately. If it is desired to simply view the radiogram, the signal is sent over line (111) and is displayed as a regular image of a radiogram (112). Alternatively, if it is desired to view the position of the exposure control sensors with the radiogram image, the sensor position information is retrieved from memory (100) and a composite of the two images (110) is sent for display to the image display (112).

Similarly, if the operator wants to see whether the patient was properly positioned relative to the radiation beam, the alignment image and coordinates are recovered from the memory (102) and a composite image of the radiogram and the alignment information is formed (110).

It is also possible to display the sensors without obscuring the information in the radiogram. This may be done by altering the display color of the radiogram pixels in the area of the control sensor without erasing the information contained in the pixels. In the alternative, display of the control sensor or collimating field indicia may be done either by adding a predetermined incremental value to the digital value of a pixel displaying image data, or by replacing the data in the pixel with a preset value representing the indicia.

Those having the benefit of the above description of my invention may provide numerous such modifications of the invention. These modifications are to be construed as being encompassed within the scope of the present invention as set forth in the appended claims wherein.

What is claimed is:

1. A method for optimizing a radiation exposure of a subject having areas presenting different radiation absorption in an imaging system comprising an imaging panel comprising a plurality of detectors providing an electrical output signal representative of the radiation intensity incident on said detectors, the imaging system further including a radiation source, a display medium and an exposure control system, the exposure control system comprising at least one exposure control sensor positioned to receive radiation directed at said subject, the method comprising:

(a) exposing the subject to radiation for a time controlled by the exposure control system;

(b) capturing with said imaging panel the exposure of the subject as an electrical signal representing an image; and (c) displaying the image on the display medium simultaneously with indicia superposed on the image, showing the relative location of the at least one exposure control sensor on the image.

2. The method according to claim 1 wherein the system further comprises a subject positioning device associated with said source of radiation, said positioning device including a visible pattern projected onto the subject for proper placement of the subject relative to the radiation source, and wherein the method further comprises superposing on the displayed image indicia representing said pattern.

3. A radiographic exposure system comprising:

a radiation imaging panel comprising an array of a plurality of detectors providing an electrical output signal representative of the radiation intensity incident on said imaging panel;

an imaging radiation source;

an exposure control system including at least one exposure control sensor positioned to receive radiation incident on said panel, wherein the exposure control system is connected to said imaging radiation source;

an image display device;

an electronic image processor connected to the imaging panel and to the image display device;

wherein said image processor processes an output from said imaging panel to display an image representing a radiation exposure of a subject located between said radiation source and said imaging panel and superposes on said displayed image indicia showing the position of at least one exposure control sensor relative to said displayed image.

4. The system according to claim 3 further comprising a targeting alignment device comprising a visible projected pattern on said subject, aligned with said radiation source, and wherein said image processor also superposes on said displayed image at least a portion of said pattern.

* * * * *